(12) United States Patent
Xing (10) Patent No.: US 9,850,544 B2
(45) Date of Patent: *Dec. 26, 2017

(54) GENETIC AMPLIFICATION OF IQGAP1 IN CANCER

(71) Applicant: THE JOHNS HOPKINS UNIVERSITY, Baltimore, MD (US)

(72) Inventor: Michael Mingzhao Xing, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/839,005

(22) Filed: Aug. 28, 2015

(65) Prior Publication Data
US 2016/0053331 A1 Feb. 25, 2016

Related U.S. Application Data

(63) Continuation of application No. 13/641,994, filed as application No. PCT/US2011/032696 on Apr. 15, 2011, now Pat. No. 9,157,123.

(60) Provisional application No. 61/326,010, filed on Apr. 20, 2010.

(51) Int. Cl.
| | |
|---|---|
| *C07H 21/04* | (2006.01) |
| *C12Q 1/68* | (2006.01) |
| *A61K 31/00* | (2006.01) |
| *A61K 31/7105* | (2006.01) |
| *A61K 31/713* | (2006.01) |
| *C12N 15/113* | (2010.01) |
| *G01N 33/574* | (2006.01) |

(52) U.S. Cl.
CPC .......... *C12Q 1/6886* (2013.01); *A61K 31/00* (2013.01); *A61K 31/713* (2013.01); *A61K 31/7105* (2013.01); *C12N 15/113* (2013.01); *G01N 33/57484* (2013.01); *C12N 2310/14* (2013.01); *C12N 2310/531* (2013.01); *C12Q 2600/118* (2013.01); *C12Q 2600/136* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 9,157,123 | B2 * | 10/2015 | Xing | A61K 31/00 |
| 2008/0312093 | A1 * | 12/2008 | Inazawa | C12Q 1/6886 |
| | | | | 506/9 |
| 2014/0088169 | A1 * | 3/2014 | Gollin | A61K 31/7088 |
| | | | | 514/44 A |

OTHER PUBLICATIONS

Corson et al. (Oncogene, vol. 24, pp. 4741-4753, 2005).*
Briggs et al (2003) IQGAP proteins are integral components of cytoskeletal regulation. EMBO Rep. Jun. 2003;4 (6):571-4.
Nojima et al (2008) IQGAP3 regulates cell proliferation through the Ras/ERK signalling cascade. Nat Cell Biol. Aug. 2008;10(8):971-8. doi: 10.1038/ncb1757. Epub Jul. 6, 2008.
Johnson et al (2009) IQGAP1 regulation and roles in cancer. Cell Signal. Oct. 2009;21(10):1471-8. doi: 10.1016/j.cellsig.2009.02.023. Epub Mar. 6, 2009.
White et al (2009) IQGAPs in cancer: a family of scaffold proteins underlying tumorigenesis. FEBS Lett. Jun. 18, 2009;583(12):1817-24. doi: 10.1016/j.febslet.2009.05.007. Epub May 9, 2009.
Ho et al (1999) IQGAP1 integrates Ca2+/calmodulin and Cdc42 signaling. J Biol Chem. Jan. 1, 1999;274(1):464-70.
Brown et al (2006) IQGAP1 in cellular signaling: bridging the GAP. Trends Cell Biol. May 2006;16(5):242-9. Epub Apr. 3, 2006.
Weissbach et al (1994) Identification of a human rasGAP-related protein containing calmodulin-binding motifs. J Biol Chem. Aug. 12, 1994;269(32):20517-21.
Roy et al (2004) IQGAP1 binds ERK2 and modulates its activity. J Biol Chem. Apr. 23, 2004;279(17):17329-37. Epub Feb. 17, 2004.
Roy et al (2005) IQGAP1 is a scaffold for mitogen-activated protein kinase signaling. Mol Cell Biol. Sep. 2005;25 (18):1940-52.
Ren et al (2007) IQGAP1 modulates activation of B-Raf. Proc Natl Acad Sci U S A. Jun. 19, 2007;104(25):10465-9. Jun. 11, 2007.
Sugimoto et al (2001) IQGAP1, a negative regulator of cell-cell adhesion, is upregulated by gene amplification at 15q26 in gastric cancer cell lines HSC39 and 40A. J Hum Genet. 2001;46(1):21-5.
Nabeshima et al (2002) Immunohistochemical analysis of IQGAP1 expression in human colorectal carcinomas: its overexpression in carcinomas and association with invasion fronts. Cancer Lett. Feb. 8, 2002;176(1):101-9.

(Continued)

*Primary Examiner* — Jeanine A Goldberg
(74) *Attorney, Agent, or Firm* — Johns Hopkins Technology Ventures (57) ABSTRACT

We examined IQGAP1 copy gain and its relationship with clinicopathologic outcomes of thyroid cancer and investigated its role in cell invasion and molecules involved in the process. We found IQGAP1 copy number (CN) gain≥3 in 1 of 30 (3%) of benign thyroid tumor, 24 of 74 (32%) follicular variant papillary thyroid cancer (FVPTC), 44 of 107 (41%) follicular thyroid cancer (FTC), 8 of 16 (50%) tall cell papillary thyroid cancer (PTC), and 27 of 41 (66%) anaplastic thyroid cancer, in increasing order of invasiveness of these tumors. A similar tumor distribution trend of CN≥4 was also seen. IQGAP1 copy gain was positively correlated with IQGAP1 protein expression. It was significantly associated with extrathyroidal and vascular invasion of FVPTC and FTC and, remarkably, a 50%-60% rate of multifocality and recurrence of BRAF mutation-positive PTC (P=0.01 and 0.02, respectively). The siRNA knockdown of IQGAP1 dramatically inhibited thyroid cancer cell invasion and colony formation. Co-immunoprecipitation assay showed direct interaction of IQGAP1 with E-cadherin, a known invasion-suppressing molecule, which was upregulated when IQGAP1 was knocked down. IQGAP1, through genetic copy gain, plays an important role in the invasiveness of thyroid cancer and represents a useful prognostic marker and therapeutic target for this and other cancers.

1 Claim, 4 Drawing Sheets

(56) References Cited

OTHER PUBLICATIONS

Dong et al (2006) Overexpression and diffuse expression pattern of IQGAP1 at invasion fronts are independent prognostic parameters in ovarian carcinomas. Cancer Lett. Nov. 8, 2006;243(1):120-7. Epub Jan. 4, 2006.
Riesco-Eizaguirre et al (2007) Molecular biology of thyroid cancer initiation. Clin Transl Oncol. Nov. 2007;9 (11):686-93.
Xing et al (2008) Recent advances in molecular biology of thyroid cancer and their clinical implications. Otolaryngol Clin North Am. Dec. 2008;41(6):1135-46, ix. doi: 10.1016/j.otc.2008.07.001.
Sobrinho-Simoes et al (2008) Intragenic mutations in thyroid cancer. Endocrinol Metab Clin North Am. Jun. 2008;37(2):333-62, viii. doi: 10.1016/j.ecl.2008.02.004.
Hundahl et al (1998) A National Cancer Data Base report on 53,856 cases of thyroid carcinoma treated in the U.S., 1985-1995 [see commetns]. Cancer. Dec. 15, 1998;83(12):2638-48.
Verburg et al (2009) Histology does not influence prognosis in differentiated thyroid carcinoma when accounting for age, tumour diameter, invasive growth and metastases. Eur J Endocrinol. Apr. 2009;160(4):619-24. doi: 10.1530/EJE-8-0805. Epub Jan. 21, 2009.
Zidan et al (2003) Pure versus follicular variant of papillary thyroid carcinoma: clinical features, prognostic factors, treatment, and survival. Cancer. Mar. 1, 2003;97(5):1181-5.
Xing et al (2007) BRAF mutation in papillary thyroid cancer: pathogenic role, molecular bases, and clinical implications. Endocr Rev. Dec. 2007;28(7):742-62. Epub Oct. 16, 2007.
Xing et al (2010) Prognostic utility of BRAF mutation in papillary thyroid cancer. Mol Cell Endocrinol. May 28, 2010;321 (1):86-93. doi: 10.1016/j.mce.2009.10.012. Epub Oct. 31, 2009.
Hou et al (2007) Genetic alterations and their relationship in the phosphatidylinositol 3-kinase/Akt pathway in thyroid cancer. Clin Cancer Res. Feb. 15, 2007;13(4):1161-70.
Wu et al (2005) Uncommon mutation, but common amplifications, of the PIK3CA gene in thyroid tumors. J Clin Endocrinol Metab. Aug. 2005;90(8):4688-93. Epub May 31, 2005.
Liu et al (2008) Highly prevalent genetic alterations in receptor tyrosine kinases and phosphatidylinositol 3-kinase/akt and mitogen-activated protein kinase pathways in anaplastic and follicular thyroid cancers. J Clin Endocrinol Metab. Aug. 2008;93(8):3106-16. doi: 10.1210/jc.2008-0273. Epub May 20, 2008.
Hou et al (2009) Induction of thyroid gene expression and radioiodine uptake in melanoma cells: novel therapeutic implications. PLoS One. Jul. 10, 2009;4(7):e6200. doi: 10.1371/journal.pone.0006200.
Ventura et al (2004) Cre-lox-regulated conditional RNA interference from transgenes. Proc Natl Acad Sci U S A. Jul. 13, 2004;101(28):10380-5. Epub Jul. 6, 2004.
Liu et al (2007) BRAF V600E maintains proliferation, transformation, and tumorigenicity of BRAF-mutant papillary thyroid cancer cells. J Clin Endocrinol Metab. Jun. 2007;92(6):2264-71. Epub Mar. 20, 2007.

Morris et al (2005) Nucleotide variants within the IQGAP1 gene in diffuse-type gastric cancers. Genes Chromosomes Cancer. Mar. 2005;42(3):280-6.
Schweppe et al (2008) Deoxyribonucleic acid profiling analysis of 40 human thyroid cancer cell lines reveals cross-contamination resulting in cell line redundancy and misidentification. J Clin Endocrinol Metab. Nov. 2008;93 (11):4331-41. doi: 10.1210/jc.2008-1102. Epub Aug. 19, 2008.
Margineanu et al (2008) Correlation between E-cadherin abnormal expressions in different types of cancer and the process of metastasis. Rev Med Chir Soc Med Nat Iasi. Apr.-Jun. 2008;112(2):432-6.
Schweppe et al (2009) Inhibition of Src with AZD0530 reveals the Src-Focal Adhesion kinase complex as a novel therapeutic target in papillary and anaplastic thyroid cancer. J Clin Endocrinol Metab. Jun. 2009;94(6):2199-203. doi: 10.1210/jc.2008-2511. Epub Mar. 17, 2009.
Abubaker et al (2008) Clinicopathological analysis of papillary thyroid cancer with PIK3CA alterations in a Middle Eastern population. J Clin Endocrinol Metab. Feb. 2008;93(2):611-8. Epub Nov. 13, 2007.
Kuroda et al (1998) Role of IQGAP1, a target of the small GTPases Cdc42 and Rac1, in regulation of E-cadherin-mediated cell-cell adhesion. Science. Aug. 7, 1998;281(5378):832-5.
Gottardi et al (2001) E-cadherin suppresses cellular transformation by inhibiting beta-catenin signaling in an adhesion-independent manner. J Cell Biol. May 28, 2001;153(5):1049-60.
Hage, et al., (2009) Rac1 activation inhibits E-cadherin-mediated adherens junctions via binding to IQGAPI in pancreatic carcinoma cells. Cell Communication and Signaling. vol. 7, No. 23.
Liu, et al., (2010) IQGAP1 plays an important role in the invasiveness of thyroid cancer. Clin Cancer Res; vol. 16, No. 24, pp. 6009-6018.
Owen, et al., (2008) The IQGAP1-Rac1 and IQGAP1-Cdc42 interactions. The Journal of Biological Chemistry, vol. 283, No. 3, pp. 1692-1704.
Takano, et al., (1999) Preoperative diagnosis of thyroid papillary and anaplastic carcinomas by real-time quantitative reverse transcription-polymerase chain reaction of oncofetal fibronectin messenger RNA. Cancer Research, vol. 59, pp. 4542-4545.
Vauhkonen, et al., (2006) DNA number aberrations in intestinal-type gastric cancer revealed by array-based comparative genomic hybridization. Cancer Genetics and Cytogenetics, vol. 167, pp. 150-154.
Walch, et al., (2008) Combined analysis of Rac1, IQGAP1, Tiam1 and E-cadherin expression in gastric cancer. Modern Pathology, vol. 21, pp. 544-552.
Yan, et al., (2009) Menin interacts with IQGAP1 to enhance intercellular adhesion of beta-cells. Oncogene, vol. 28, pp. 973-982.
International Search Report dated Feb. 9, 2012 for PCT/US2011/032696 filed Apr. 15, 2011.

* cited by examiner

GENETIC AMPLIFICATION OF IQGAP1 IN CANCER

CROSS-REFERENCE TO RELATED APPLICATIONS

This application is a Continuation of U.S. patent application Ser. No. 13/641,994, filed Nov. 19, 2012, which is a 35 U.S.C. §371 U.S. national entry of International Application PCT/US2011/032696, having an international filing date of Apr. 15, 2011, which claims the benefit of U.S. Provisional Application No. 61/326,010, filed Apr. 20, 2010, the content of each of the aforementioned applications is herein incorporated by reference in their entirety.

This invention was made using a grant from the U.S. National Institutes of Health. The U.S. government therefore retains certain rights in the invention, according to the terms of NIH RO-1 grant CA113507.

TECHNICAL FIELD OF THE INVENTION

This invention is related to the area of cancer prognosis and therapeutics. In particular, it relates to a gene that is amplified in human cancers

BACKGROUND OF THE INVENTION

The human IQGAP protein family comprises three members, which, as scaffold proteins, play important roles in the regulation/modulation of cytoskeletal architecture and cell adhesion through binding to various effectors/regulators (1-4). Among these, IQGAP1 has been best characterized (3-6). This protein was initially identified in human osteosarcoma cells and consists of a 1,657-amino acid polypeptide with significant similarity to the Ras-related GTPase-activating (RasGAP) proteins (7). A unique structural feature of IQGAP proteins is their IQ domain, which contains about 25 amino acids and is found in diverse families of calmodulin-binding proteins. This motif is capable of effecting on intracellular Ca2+ signaling and a wide range of cellular activities. Some previous studies showed that IQGAP1 might be able to modulate the Ras→Raf→MEK-→MAP kinase/ERK pathway (MAP kinase pathway) in certain cells, but it can also function independently of this mechanism (8-10). Overexpression of IQGAP1 was seen in certain cancers, suggesting a role of this molecule in human tumorigenesis (3,4,11-13). IQGAP3 may potentially also have such a role as it was shown to be involved in cell proliferation (2). IQGAP2 has been less well studied and may function as a tumor suppressor (4).

Follicular epithelial cell-derived thyroid cancer is a common endocrine malignancy (14). This cancer can be histologically classified into papillary thyroid cancer (PTC), follicular thyroid cancer (FTC), and anaplastic thyroid cancer (ATC). PTC can be further classified into several variants or subtypes, including mainly conventional PTC (CPTC), follicular variant PTC (FVPTC), and tall cell PTC (TCPTC). A striking genetic alteration in PTC is the BRAF mutation, which plays an important oncogenic role through activation of the MAP kinase pathway (15-17). ATC is a rare but rapidly lethal cancer with aggressive invasion and metastasis. PTC and FTC are both differentiated thyroid cancers with a relatively indolent clinical course, but FTC is generally more invasive and aggressive than PTC except for certain types, such as TCPTC, which is also relatively aggressive (18, 19). FTC and FVPTC tend to display invasive behaviors, such as vascular invasion (20). It is not known whether IQGAP proteins play any role in thyroid tumorigenesis or whether it determines aggressiveness our outcome in other cancers. There is a continuing need in the art to obtain better tools for diagnosing, prognosing, and treating human cancers.

SUMMARY OF THE INVENTION

According to one aspect of the invention a method is provided for categorizing a human tissue sample. An increased copy number of IQGAP1 in the tissue sample is detected relative to its copy number in normal tissue or relative to copy number of a reference gene in the tissue sample. The tissue sample is then assigned to a group based on its IQGAP1 copy number.

According to another aspect of the invention a method is provided for treating a human cancer. An inhibitor of IQGAP1 protein or its expression is administered to a patient with cancer. The treatment can diminish the invasiveness or spread of the cancer.

According to yet another aspect of the invention a method is provided for identifying candidate drugs for treating human cancers that have a copy number of IQGAP1 of greater than 2. A test substance is contacted with IQGAP1 and E-cadherin. A test substance that inhibits binding of IQGAP1 to E-cadherin is identified as a candidate drug for treating a human cancer that has a copy number of IQGAP1 of greater than 2.

These and other embodiments which will be apparent to those of skill in the art upon reading the specification provide the art with ways to stratify, categorize, and treat cancers on the basis of genetic characteristics.

BRIEF DESCRIPTION OF THE DRAWINGS

FIGS. 1A-1C show immunohistostaining (IHS) of IQGAP1 in thyroid cancer. Presented are representative tumor samples with various IQGAP1 copy numbers (CNs) and corresponding IHS of the IQGAP1 protein. A brown color of staining using anti-IQGAP1 antibodies represented IQGAP1 protein. Cases A, B, and C represent IHS scores I, II, and III, respectively, as defined in Example 1. Corresponding IQGAP1 CNs are indicated in the brackets.

FIGS. 2A-2B show effects of shRNA knockdown of IQGAP1 or IQGAP3 on the invasion of thyroid cancer cells. SW1736, KAT18, and FTC133 cells, at a density of 2.5×104 cells/well, were seeded on Matrigel invasion chamber plates and cultured in routine medium for 22 hours. Invasive cells that penetrated through pores and migrated to the underside of the membrane were stained by crystal violet and photographed under a microscope. FIG. 2 B is a histogram plots of the number of invading cells corresponding to FIG. 2A for each cell type. "(C)" denotes cell transfection with shRNA containing scrambled nucleotides; "(S)" denotes cell transfection with specific shRNA to knock down IQGAP1 or IQGAP3. **, P<0.01.

FIGS. 3A-3B. Effects of shRNA knockdown of IQGAP1 and IQGAP3 on anchorage-independent colony formation of thyroid cancer cells. SW1736 and FTC133 cells stably transfected with control shRNA or specific shRNA to knock down IQGAP1 or IQGAP3 were seeded in 6-well plates in 0.3% agar over a bottom layer of 0.6% agar and treated with routine medium plus 1.5 mg/mL puromycin. After 2-3 weeks, cell colony numbers were counted under microscope and cell colonies were photographed.

FIGS. 4A-4B shows western blotting and immunoprecipitation (IP) analysis of the relationship of IQGAP1 with other signaling molecules in thyroid cancers. Thyroid cancer cell lines with stable transfections were lysed for Western blotting after 24 hours of serum starvation.

DETAILED DESCRIPTION OF THE INVENTION

The inventor has investigated the oncogenic role of IQGAP1 in cancer and its potential as a prognostic marker and therapeutic target in cancer. A genetic copy gain of IQGAP1 was found to be associated with increased invasiveness and aggressiveness of thyroid cancer. IQGAP1 genetic copy gain was preferentially seen in aggressive types of thyroid cancer and highly associated with extra-thyroidal and vascular invasion. In BRAF mutation-positive papillary thyroid cancer (PTC), IQGAP1 copy gain was associated with a tumor recurrence rate of 60%. In vitro knockdown of IQGAP1 dramatically inhibited thyroid cancer cell invasion. The clinical implications of these results are at least two: (i) IQGAP1 copy gain can be used to predict invasiveness and aggressiveness of thyroid cancer and, when coexisting with BRAF mutation is a particularly powerful predictor for cancer recurrence; (ii) IQGAP1 represents a therapeutic target for cancers, including thyroid cancers.

Copy number gain may be assessed by any means known in the art. These include without limitation, FISH (fluorescent in situ hybridization), In situ hybridization, Molecular cytogenetics, Virtual Karyotype, Happy mapping, Single Molecule RNA, Fiber FISH, Q-FISH, Flow-FISH, and digital karyotyping. Variations and alternatives to these techniques can be used. The gain can be measured using either a reference gene in the same tissue as the test tissue or using the IQGAP1 gene in a reference (normal) tissue. The amplification that has been observed has been relatively modest, with copy numbers of greater than 2, greater than 3, or greater than 4, although larger gains are possible, such as greater than 5, 6, 7, 8, 9, or 10 copies.

IQGAP1 is the official symbol for the gene named IQ motif containing GTPase activating protein 1 in *Homo sapiens*. Other names for this gene include HUMORFA01, KIAA0051, SARI, p195, RasGAP-like with IQ motifs; and ras GTPase-activating-like protein IQGAP1. The gene is located on chromosome 15 at location: 15q26.1 in the human genome. Its annotation is chromosome 15, NC_000015.9 (90931473 . . . 91045475). The protein contains four IQ domains, one calponin homology domain, one Ras-GAP domain and one WW domain. It interacts with components of the cytoskeleton, with cell adhesion molecules, and with several signaling molecules to regulate cell morphology and motility. See NP_003861.

Human tissue samples which can be tested include any that are suspected of being neoplastic. These include thyroid, lung, colorectal, ovarian, melanoma, acute lymphocytic leukemia (white blood cells), glioblastoma, hepatocellular carcinoma, prostate, and pancreas. Other tissues which may be tested are skin, liver, kidney, head and neck, lymph tissue, cervix, testes, uterus, esophagus, and brain. Tissue samples can be obtained by any means known in the art, including without limitation, by biopsy, by aspiration, or from a surgical sample.

Groups that are formed based on the copy number may be either copy number gain or no gain. They may be further divided based on the amount of gain that is observed. For example, tissues that have a greater than 4 may be put in a separate group from those with a copy gain of 2. In addition, groups can be formed based on this factor in addition to other factors. Other factors may be independent prognostic or diagnostic factors, including age, gender, ethnic origin, other genetic markers, smoker, family cancer history, environmental exposure to carcinogens, etc. One such other factor is a BRAF mutation which is prevalent in certain tumors. The most prevalent of the mutations is T1796A (V600E). This mutation synergizes with IQGAP1 mutations, particularly in leading to a more aggressive tumor phenotype. Groups that are formed based on the presence or absence of copy number gain or the amount of gain of copy number can be used used to formulate and/or provide a prognosis, to formulate and/or provide a diagnosis, to prescribe a treatment, to prescribe a monitoring schedule, and to stratify patients in a clinical trial. Typically, formulating a treatment, diagnosis, or prognosis will be done using tools such as graphs, computer programs, data tables, etc. More than a mere mental act is required. The treatment, diagnosis, prognosis, etc. will typically be recorded on a storage medium. The treatment, diagnosis, prognosis, etc. will typically be communicated to a patient or to other medical personnel.

Human cancers can be treated using one or more inhibitors of IQGAP1 protein or its expression. Suitable inhibitors include an inhibitory RNA molecule, such as a siRNA, an antisense RNA, an antisense DNA construct, and an antibody, whether polyclonal, monoclonal, fragmented, single chain, chimeric, hybrid, etc. Cancers which are amenable to such treatments include without limitation: thyroid, lung, colorectal, ovarian, melanoma, acute lymphocytic leukemia (white blood cells), glioblastoma, hepatocellular carcinoma, prostate, head and neck, brain, pancreas, skin, liver, kidney, head and neck, lymph tissue, cervix, testes, uterus, esophagus, and brain. In some cases the human cancers have been tested and determined to have a copy number greater than 2 of IQGAP1, copy number greater than 3 of IQGAP1, copy number greater than 4 of IQGAP, a BRAF mutation, and combinations of one of said IQGAP copy numbers and a BRAF mutation. In other cases the testing for copy number and/or BRAF is used prior to the treatment to determine eligibility and likely benefit.

Candidate drugs can be identified for treating human cancers that have a copy number greater than 2, 3, or 4 of IQGAP1. A test substance is contacted with IQGAP1 and E-cadherin. The contacting can be done in vitro or in cells, such as in a two-hybrid assay, for example. A test substance that inhibits binding of IQGAP1 to E-cadherin is identified as a candidate drug for treating a human cancer that has a greater than 2, 3, or 4 copy number of IQGAP1. A candidate drug can be further tested for its ability to affect growth, invasiveness, or spread of a human cancer that has a greater than 2, 3, or 4 copy number of IQGAP1. Such tests can be done advantageously in animal models, such as in a mouse with a human xenograft. The human xenograft will have an appropriate copy number gain of IQGAP1. Cancers which may be used to test or as ultimate recipients of a drug include without limitation, thyroid, lung, colorectal, ovarian, melanoma, acute lymphocytic leukemia (white blood cells), glioblastoma, hepatocellular carcinoma, prostate, head and neck, brain, pancreas, skin, liver, kidney, head and neck, lymph tissue, cervix, testes, uterus, esophagus, and brain.

Genomic IQGAP1 copy gain is found in thyroid cancers, with a preferential association with invasive types of thyroid cancer, such as, ATC, TCPTC, and FTC. The IQGAP1 gene is located at 15q26, a chromosome area that is frequently amplified in many human malignancies, but contains a number of genes. IQGAP1 expression is enhanced in many cancers (4) and was associated with IQGAP1 copy number gain in gastric cancer cell lines (11). The IQGAP1 copy gain is a gene-specific event in thyroid cancer; IQGAP3 did not show copy gain. Moreover, only rare copy gain of TMEM84 was observed, a gene that is located at 15q23, about 20 Mb from IQGAP1 in the same chromosome, in striking contrast with the frequent copy gain of the IQGAP1 gene. Therefore, IQGAP1 copy gain in thyroid cancer is likely due to the amplification of the gene rather than aneuploidy. The fact that IQGAP1 copy gain was associated with protein expression and poorer clinicopathologic outcomes provides strong support for the functional relevance of this genetic alteration. This also suggests that IQGAP1 copy gain in thyroid cancer is sufficient to play a significant amplifying role in the pathway cascade involving IQGAP1.

It is interesting that IQGAP1 copy gain-associated tumor invasiveness occurred mainly in FTC and FVPTC among the thyroid tumors. It is well known that invasion, including vascular invasion, is a particularly strong feature of these follicular types of thyroid cancer. The association of IQGAP1 copy gain with thyroid cancer invasion and aggressiveness is consistent with previous reports of over-expression of IQGAP1 in the invasion fronts of some cancers, such as, colorectal cancer (12) and ovarian cancer (13). Our in vitro studies using ATC- and FTC-derived cancer cell lines further support a role of IQGAP1 in thyroid tumorigenesis by showing remarkable inhibition of cell invasion in in vitro assays and reduction of colony formation on soft agar of thyroid cancer cells by IQGAP1 knockdown. These in vitro data are consistent with and support the clinicopathologic correlation findings of IQGAP1 in thyroid cancers in this study. The contrasting infrequent copy gain of the IQGAP3 gene and the lack of a role of IQGAP3 in cell colony formation and invasion support the specific role of IQGAP1 in thyroid tumorigenesis.

Promotion of cell growth and proliferation may not be the major effect of IQGAP1 in cancer. This is consistent with the inability of IQGAP1 to interact with the MAP kinase and PI3K/Akt pathways in thyroid cancer cells, which are major signaling pathways that promote thyroid cancer cell proliferation (15-17). In this regard, thyroid cancer cells are different than some other cancer cells in which IQGAP1 may interact with the MAP kinase pathway (8-10). However, upregulated IQGAP1 system through IQGAP1 copy gain and aberrant activation of the MAP kinase pathway through BRAF mutation may synergistically promote a poor clinical course of PTC; BRAF mutation-positive PTC, but not BRAF mutation-negative PTC, demonstrated an association between IQGAP1 copy gain and tumor multifocality and recurrence. BRAF mutation's well established role in the aggressiveness of PTC (22), is consistent with its synergism with the invasiveness-promoting IQGAP1 copy gain and poor clinical outcome. This phenomenon is similar to the previously reported association of PIK3CA gene copy gain with increased recurrence of thyroid cancer when coexisting with BRAF mutation (33). The prevalence of BRAF mutation in PTC is relatively high, around 45% on average (21, 22). It may be possible to use the combination of the two genetic markers to identify a small group of PTC patients with a particularly high risk of recurrence for more aggressive treatments.

The transmembrane protein E-cadherin was shown to directly interact with the IQGAP1 protein in thyroid cancer cells, as similarly seen in some other cells (34). Interestingly, an upregulation of E-cadherin protein results from IQGAP1 knockdown in thyroid cancer cells, suggesting that IQGAP1 normally functions to negatively regulate E-cadherin in thyroid cancer cells. Over-expression of IQGAP1 through IQGAP1 copy gain may thus be expected to cause down-regulation of E-cadherin in thyroid cancer cells although we did not directly test this. An important function of E-cadherin is to enhance cell adhesion and prevent proteolytic degradation of the surrounding tissue and inhibit cell motility, thus preventing cancer cells from invading and metastasizing (31). E-cadherin was also reported to be able to suppress transformation of colorectal cells (35), consistent with the inhibition of colony formation of thyroid cancer cells on soft agar induced by IQGAP1 knockdown in this study. Thus, disruption of E-cadherin may be an important mechanism underlying the association of IQGAP1 copy gain with the invasiveness and aggressiveness of thyroid cancers and, conversely, the inhibition of cell invasion and anchorage-independent colony formation of SW1736 cells by IQGAP1 knockdown. Obviously, other mechanisms remain to be also identified.

IQGAP1 plays an important role in the invasiveness and aggressiveness of cancer through genomic IQGAP1 copy gain, which is consistent with the role of IQGAP1 in cancer cell invasion and anchorage-independent colony formation as well as the direct interaction of IQGAP1 with E-cadherin and the negative effect of the former on the expression of the latter. IQGAP1 copy gain synergizes with BRAF mutations to promote a poorer clinical outcome.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1—Materials and Methods

Genomic DNA Isolation from Thyroid Tumor Specimens

A total of 383 thyroid tumor samples were analyzed for this study, including 30 benign tumors, 205 PTC, 107 FTC, and 41 ATC, which were originally obtained and prepared for genomic DNA isolation with institutional review board approvals (23). In brief, after xylene treatment to remove paraffin, tissues were digested with sodium dodecyl sulfate-proteinase K and DNA was subsequently isolated following standard phenol-chloroform extraction and ethanol precipitation protocols.

Analysis of IQGAP1 Mutation in Thyroid Tumor Samples

Genomic DNA sequencing was done for IQGAP1 mutation analysis. We selected exons 19 to 23 and exon 29 for mutation analysis, as they constitute the IQ domain of IQGAP1 or sometimes harbored mutations in other cancers. Genomic DNA was amplified by PCR, using standard reaction conditions.

Analysis of Genomic Copy Gain of the IQGAP Genes with Quantitative Real-Time PCR Quantitative real-time PCR was used to analyze copy number (CN) of IQGAP1 and 3 genes using the ABI 7900HT PCR system (Applied Biosystems). This is a widely used and robust technique for genomic CN analysis, for which we use our well-established FISH-proven protocol as detailed previously (23-26). Specific primers and probes were designed using Primer Express 3.0 (Applied Biosystem) to amplify and detect IQGAP1, IQGAP3, TMEM84, and β-actin genes. The probes were labeled with 5' fluorescent reporter dye (6FAM) and 3' quencher dye (TAMRA). β-Actin was run in parallel to standardize the input DNA. Standard curve was established using normal leukocyte DNA with a quantity range of 0.02-10 ng/µL.

Analysis of IQGAP1 Protein Expression by Immunohistostaining

Immunohistostaining (IHS) was done using a modified protocol (23). In brief, thyroid tumor tissue sections were dewaxed, soaked in alcohol, and incubated in 3% hydrogen peroxide for 15 minutes to inactivate endogenous peroxidase activity after microwave treatment in an antigen-unmasking solution (Vector Lab). Tissue sections were incubated overnight at 4° C. with anti-IQGAP1 antibody (BD Biosciences). Immunostaining was done with Vectastain Universal Quick kit (Vector Lab) following the manufacturer's protocol. Peroxidase activity was revealed using 3,3-diaminobenzidine. Negative control was obtained by omission of primary antibodies. We classified IHS into 3 levels represented by scores I-III: IHS score I, staining of <10% of cells; IHS score II, staining of 10%-50% of cells; IHS score III, staining of >50% of cells.

Thyroid Cancer Cell Lines

Three human thyroid cell lines used in this study were as follows: the ATC cell lines SW1736 and KAT18 were originally from Dr. N. E. Heldin (University of Uppsala) and Dr. Kenneth B. Ain (University of Kentucky Medical Center), respectively; and the FTC cell line FTC133 was from Dr. Georg Brabant (Christie Hospital). They were provided by Drs. Rebecca Schweppe and Bryan Haugen (University of Colorado). Cells were cultured and maintained as described previously (26).

shRNA Plasmid Construction

Specific and scrambled control shRNAs were designed using an online program of Invitrogen Corp (rnadesigner). The shRNA target sequence for IQGAP1, GCATCCACT-TACCAGGATA(SEQ ID NO: 1), located from 763 to 781 nt (nucleotide) of the IQGAP1 cDNA (with the translation start site set as +1), was selected for IQGAP1 gene knockdown. The corresponding nonspecific shRNA duplex containing the same nucleotide composition but in random sequence (scrambled) were used as control: GCCACCCATA-GAAATTTCG (SEQ ID NO: 2). The shRNA target sequence for IQGAP3, GGACCTGAGCAAGCTAGAA (SEQ ID NO: 3), located from 4,005 to 4,023 nt of the IQGAP3 cDNA was selected for specific knockdown, and the corresponding nonspecific scrambled shRNA duplex (GCCAACGGACGTAATGAAG; SEQ ID NO:4) were used as control. There were 2 complementary oligonucleotides, T-(target or control sense)-TTCAAGAGA(SEQ ID NO: 5). -(target or control antisense)-TTTTTTC(SEQ ID NO: 6). and TCGAGAAAAAA(SEQ ID NO: 7). -(target or control sense)-TCTCTTGAA(SEQ ID NO: 8). -(target or control antisense)-A, synthesized for each target or control sequence and annealed in vitro. The annealed double-stranded oligonucleotides were cloned into the HpaI and XhoI sites of shRNA lentiviral expressing vector pSicoR-PGK-puro (Addgene Corp.; ref. 27) and confirmed by sequencing.

Lentiviral Mediated Gene Knockdown

The lentiviral shRNA-expressing vector, the packaging plasmid PSPAX2, and the VSV-G envelope protein-coding plasmid pMD2G were cotransfected to HEK293T cells, using Lipofectamine 2000 (Invitrogen) according to the manufacturer's protocol. After transfection for 48 hours, cellular supernatants were harvested and filtrated by passing through filters with pore size of 45 µm. The lentiviral supernatants were used to infect thyroid cancer cells. For stable transfection, the transformants were selected in medium containing 1.5 mg/mL puromycin for about 2 weeks. Stable cell clones were confirmed by Western blotting analysis.

Western Blotting Analysis

Routine Western blotting procedures were followed as described previously (26), using various primary antibodies, including anti-IQGAP1, anti-IQGAP3, anti-E-cadherin, or anti-cdc42 (BD Biosciences); anti-phospho-ERK, anti-phospho-Akt, or anti-actin (Santa Cruz Biotechnology); anti-phospho-FAK (Invitrogen); or anti-phospho-Src (Cell Signaling Technology).

Cell Proliferation Study

Cells (800/well) were seeded in quadruplets into a 96-well plate and cultured with 2.5% serum. MTT assay was carried out daily over a course of 5-6 days to evaluate cell proliferation as detailed previously (28).

Cell Invasion Assay

The invasion assay was carried out using Growth Factor Reduced Matrigel invasion chambers with 8.0-µm polycarbonated filters (BD Biosciences). In brief, 2.5×10$^4$ cells were seeded on chamber plates and cultured in routine medium. After an incubation of 22 hours at 37° C. in a humidified incubator with 5% CO2, nonmigratory cells on the upper surface of the filter were removed by wiping with a cotton swab. Invasive cells that penetrated through pores and migrated to the underside of the membrane were stained with crystal violet and counted and photographed under a microscope.

Anchorage-Independent Colony Formation Assay

For colony formation assay to examine anchorage-independent cell growth in soft agar, cells (1×10$^4$ cells/well) were plated into 6-well plates in growth medium containing 10% FBS, 1.5 mg/mL puromycin, and 0.3% agar, on top of 0.6% agar gel. After 2-3 weeks of culture, colonies were counted and photographed under a microscope (28).

Immunoprecipitation Assay

Immunoprecipitation (IP) was carried out using the Protein G Immunoprecipitation Kit (Roche Applied Science) with slight modifications. In brief, 1 mL cell lysates were precleared with 50 μL, homogeneous Protein G-agarose suspension for 6 hours. After centrifugation, the supernatants were divided into equal aliquots (about 0.5 mL of each) and incubated overnight with either mouse monoclonal anti-IQGAP1 antibody (BD Biosciences) or purified mouse IgG (Sigma-Aldrich Corp.) as control. The immune complexes were incubated with 50 μL, Protein G-agarose suspension for 6 hours, followed by 5 washings with lysis buffer, resuspension in SDS buffer, and analysis by SDS-polyacrylamide gel electrophoresis and Western blotting.

Statistical Analysis

Chi-square test was used to analyze the relationship of IQGAP1 copy gain with IHS scores, BRAF mutation, tumor recurrence, lymph node metastasis, multifocality, and extrathyroidal extension status. Fisher's exact test was used when the number of data was less than 5. Student's t test was used to analyze the relationship of IQGAP1 copy gain with patient age and tumor size. Wilcoxon's rank-sum test was used when data was not in normal distribution. Linear regression was used to analyze the relationship between IQGAP1 CN and patient age, tumor stage, and tumor size. The professional statistical software SPSS 10.0 (SPSS Inc.) was used in these analyses. P values <0.05 were considered significant.

of whether the cutoff value of CN≥3 or CN≥4 was used to define copy gain. Among the 3 subtypes of PTC, the most aggressive TCPTC has the highest rate of IQGAP1 copy gain when the cutoff CN≥3 was used in the analysis (up to 50%). We also studied the CN of IQGAP1 in 30 benign thyroid tumors and 30 normal thyroid tissue samples. Among all these samples, only 1 case of benign tumor was identified with copy gain when a cutoff CN≥3 was used. Therefore, a clear trend of association between IQGAP1 copy gain and the known order of increasing aggressiveness of these thyroid cancers was showed, suggesting an important role of IQGAP1 copy gain in thyroid tumorigenesis. Fifteen of those normal thyroid tissue samples had matched PTC tumor samples and 4 (27%) of these 15 matched PTC had IQGAP1 copy gain. These results showed the malignancy specificity of IQGAP1 copy gain. We also examined the CN of the TMEM84 gene, which is located at 15q23 and about 20 Mb away from the IQGAP1 gene in the same chromosome. Only 1 of 60 (1.7%) cases examined, including 30 PTC and 30 FTC, was found to have TMEM84 copy gain. This result suggests that IQGAP1 copy gain in these cancers represented mainly genetic amplification, not chromosome number gain. For the IQGAP3 gene, copy gain was seen only in 4/38 (10.5%) ATC, 4 of 39 (10.3%) FTC, and 4 of 85 (4.7%) PTC when using CN≥3 as the cutoff value, and 1 of 38 (2.6%) ATC, 0 of 39 (0%) FTC, and 2 of 85 (2.4%) PTC, when using CN≥4 as the cutoff value. Thus, unlike IQGAP1, copy gain of IQGAP3 is uncommon and does not play a major role in thyroid tumorigenesis.

TABLE 1

| | IQGAP1 and IQGAP3 copy gain in thyroid cancers [n/N (%)] | | | |
|---|---|---|---|---|
| | IQGAP1 CN | | IQGAP3 CN | |
| | ≥3.0 | ≥4.0 | ≥3.0 | ≥4.0 |
| ATC | 27/41 (65.9) | 14/41 (34.1) | 4/38 (10.5) | 1/38 (2.6) |
| FTC | 44/107 (41.1) | 24/107 (22.4) | 4/39 (10.3) | 0/39 (0) |
| PTC | | | | |
| All | 72/205 (35.1) | 27/205 (13.2) | 4/85 (4.7) | 2/85 (2.4) |
| CPTC | 40/115 (34.8) | 17/115 (14.8) | 2/54 (3.7) | 1/54 (1.9) |
| FVPTC | 24/74 (32.4) | 8/74 (10.8) | 2/25 (8) | 1/25 (4) |
| TCPTC | 8/16 (50) | 2/16 (12.5) | 0/6 (0) | 0/6 (0) |

Abbreviations:
n, the number of cases with the indicated IQGAP CN;
N, the number of cases examined.

Example 2—Uncommon Mutation but Common Genetic Copy Gain of the IQGAP1 Gene in Thyroid Cancers A M1231I IQGAP1 mutation was occasionally seen in certain human cancers (29). We examined this mutation in 70 thyroid tumor samples but found only 1 case (1.4%) to harbor this mutation. We also examined exons 19 to 23, which constitute the functionally important IQ domain of IQGAP1, for possible mutation, and found no mutation in 70 thyroid tumor samples. Therefore, mutation of the IQGAP1 gene does not seem to be a major mechanism in thyroid cancer.

Figure 1A:
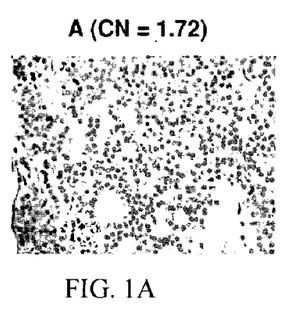
Figure 1B:
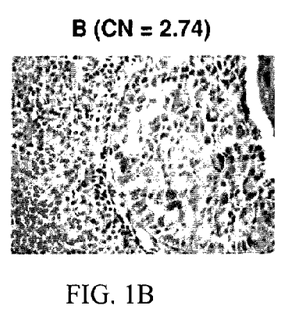
Figure 1C:
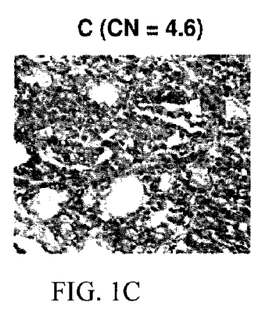

As tumor-promoting genes often gain CN in thyroid cancer (25), we analyzed IQGAP1 and IQGAP3 CN in various types of thyroid cancers. As shown in Table 1, IQGAP1 copy gain was common in thyroid cancers, seen in 66% and 41% of ATC and FTC, respectively, when the CN≥3 was used as the cutoff value. The highest copy gain rate was seen in ATC, followed by FTC, and PTC regardless Example 3—Association of IQGAP1 Copy Gain with Increased Expression of IQGAP1 Protein in Thyroid Cancers To show the biological relevance of genetic copy gain of the IQGAP1 gene in thyroid cancer, we investigated the impact of this genetic alteration on the expression of IQGAP1 protein by IHS analysis using IQGAP1-specific antibodies on 29 FTC samples that had available histopathologic slides. FIG. 1 shows representative tumor samples illustrating the IHS scores and corresponding IQGAP1 CNs. Among the 9 cases without IQGAP1 copy gain (CN<3), 6 (66.7%) had a IHS score I, 2 (22.2%) had a score II, and 1 (11.1%) had a score III, whereas among the 20 cases with IQGAP1 copy gain (CN≥3), only 1 (5%) had a IHS score I, but 10 (50%) and 9 (45%) had cores II and III, respectively, with a significant difference between the 2 groups on overall analysis (P<0.01). To take a further look at specific groups, IHS score I was seen in 6 of 9 (66.7%) of the cases with CN<3 versus 1 of 20 (5%) of the cases with CN≥3

(P<0.001). Conversely, IHS scores II and III, in combination, were seen in 3 of 9 (33%) of the cases with CN<3 versus 19 of 20 (95%) of the cases with CN≥3 (P<0.001).

not shown). Patient age and gender, tumor size, and lymph node metastasis were not significantly associated with IQGAP1 copy gain (data not shown).

TABLE 2

Relationship or IQGAP1 copy gain with clinicopathologic outcomes of thyroid cancers [n/N (%)]

| Tumor types | Clinicopathologic characteristics | Cutoff CN ≥3.0 | | | Cutoff CN ≥4.0 | | |
|---|---|---|---|---|---|---|---|
| | | Copy gain (+) | Copy gain (−) | P value | Copy gain (+) | Copy gain (−) | P value |
| FTC | Extrathyroidal invasion | 12/28 (42.9) | 6/35 (17.1) | 0.03 | 6/12 (50) | 12/51 (23.5) | 0.07 |
| | Vascular invasion | 18/28 (64.3) | 12/35 (34.3) | 0.02 | 9/12 (75) | 21/51 (41.2) | 0.05 |
| | Cancer multifocality | 2/29 (6.9) | 1/35 (2.9) | 0.59 | 1/13 (7.7) | 2/51 (3.9) | 0.5 |
| | Tumor recurrence | 3/29 (10.3) | 8/35 (22.9) | 0.32 | 2/13 (15.4) | 9/51 (17.6) | 1 |
| PTC (all) | BRAF mutation | 30/71 (42.3) | 56/132 (42.4) | 0.98 | 11/26 (42.3) | 75/177 (42.4) | 0.99 |
| | Extrathyroidal invasion | 23/71 (32.4) | 38/132 (28.8) | 0.59 | 9/26 (34.6) | 52/177 (29.4) | 0.59 |
| | Cancer multifocality | 28/71 (39.4) | 54/132 (40.9) | 0.84 | 10/26 (38.5) | 72/177 (40.7) | 0.83 |
| | Tumor recurrence | 12/60 (20) | 20/113 (17.7) | 0.71 | 7/24 (29.2) | 25/149 (16.8) | 0.15 |
| CPTC | BRAF mutation | 19/39 (48.7) | 45/75 (60) | 0.25 | 8/16 (50) | 56/98 (57.1) | 0.59 |
| | Extrathyroidal invasion | 15/39 (38.5) | 30/75 (40) | 0.87 | 5/16 (31.3) | 40/98 (40.8) | 0.47 |
| | Cancer multifocality | 18/39 (46.2) | 33/75 (44) | 0.83 | 8/16 (50) | 43/98 (43.9) | 0.65 |
| | Tumor recurrence | 6/31 (19.4) | 14/61 (23) | 0.69 | 3/15 (20) | 17/77 (22.1) | 0.86 |
| FVPTC | BRAF mutation | 5/24 (20.8) | 4/49 (8.2) | 0.14 | 2/8 (25) | 7/65 (10.8) | 0.25 |
| | Extrathyroidal invasion | 4/24 (16.7) | 2/49 (4.1) | 0.09 | 3/8 (37.5) | 3/65 (4.6) | 0.02 |
| | Cancer multifocality | 7/24 (29.2) | 18/49 (36.7) | 0.52 | 1/8 (12.5) | 24/65 (36.9) | 0.25 |
| | Tumor recurrence | 2/21 (9.5) | 4/44 (9.1) | 0.72 | 2/7 (28.6) | 4/58 (6.9) | 0.12 |
| PTC (w/BRAF) | Tumor recurrence | 9/25 (36) | 11/48 (22.9) | 0.23 | 6/10 (60) | 14/63 (22.2) | 0.02 |
| CPTC (w/BRAF) | Cancer multifocality | 10/19 (52.6) | 18/45 (40) | 0.35 | 4/8 (50) | 4/56 (7.1) | 0.01 |

Abbreviations:
n, the number of cases positive for the indicated clinicopathologic characteristics;
N, the number of cases examined These data clearly showed an association of IQGAP1 copy gain with increased expression of the IQGAP1 protein in thyroid cancer, showing that this IQGAP1 copy gain was biologically relevant with respect to expected increase in IQGAP1 expression.

Example 4—Association with Other Mutations

We did not find a significant association of BRAF mutation with IQGAP1 copy gain either in the total PTC cohort or within the subgroup of CPTC or FVPTC, suggesting that IQGAP1 copy and BRAF mutation were two independent genetic events (Table 2). TCPTC could not be analyzed due to the relatively small number of cases. Similarly, we did not find an association of Ras mutations with IQGAP1 copy gain. Specifically, we found Ras mutations in 3 of 25 (12%) cases of samples with IQGAP1 copy gain versus 4 of 38 (11%) cases of samples without IQGAP1 copy gain (P=0.9). Although not statistically significant, a strong trend for the association of IQGAP1 copy gain with recurrence of PTC (overall cases) was noted when the cutoff CN≥4 was used (Table 2). Interestingly, when we divided the PTC samples into BRAF mutation-positive and -negative groups, IQGAP1 copy gain was significantly associated with tumor recurrence in the BRAF mutation-positive group. Specifically, 14 of 63 (22.2%) cases without IQGAP1 copy gain versus 6 of 10 (60%) cases with copy gain were associated with tumor recurrence (P=0.02) when the cutoff CN≥4 was used. A significant association of IQGAP1 copy gain with tumor multifocality was observed in CPTC that harbored BRAF mutation. Specifically, 4 of 56 (7.1%) cases without IQGAP1 copy gain versus 4 of 8 (50%) cases with copy gain were associated with multifocality (P=0.01) when the cutoff CN≥4 was used. These associations of IQGAP1 copy gain were not observed in BRAF mutation-negative PTC (data Example 5—Effects of shRNA Knockdown of IQGAP Proteins on the Signaling of MAP Kinase and PI3K/Akt Pathways and Proliferation of Thyroid Cancer Cells As MAP kinase and PI3K/Akt pathways played an important role in promoting thyroid cancer cell proliferation (15-17), we next examined whether IQGAP proteins were involved in these signaling pathways in thyroid cancer cells. We used the lentiviral-mediated-specific shRNA-expression system to stably knock down the expression of IQGAP proteins in SW1736, KAT18, and FTC133 cells that have been documented to be unique thyroid cancer cell lines (30). Although there was no IQGAP1 or IQGAP3 copy gain in these cells (date not shown), we reasoned that if IQGAP proteins normally had a significant influence on these pathways, alteration in their expression should affect their signaling. IQGAP1 expression was nearly completely knocked down in all the 3 cells whereas the control cells stably transfected with nonspecific shRNA maintained normal expression of IQGAP1. The p-ERK level was only slightly reduced in FTC133 cells and was not changed at all in SW1736 and KAT18 cells with IQGAP1 knockdown. There was no change in p-Akt in any of these cells after IQGAP1 knockdown. Using this approach, we also successfully and stably knocked down the IQGAP3 in these cells and observed no effect on p-ERK and p-Akt. Therefore, IQGAP proteins did not seem to play a significant role in the MAP kinase and PI3K/Akt pathways in thyroid cancer. Consistent with this observation, was the lack of significant effects of knockdown of IQGAP1, as well as IQGAP3, on the proliferation of these cells.

Figure 2A:
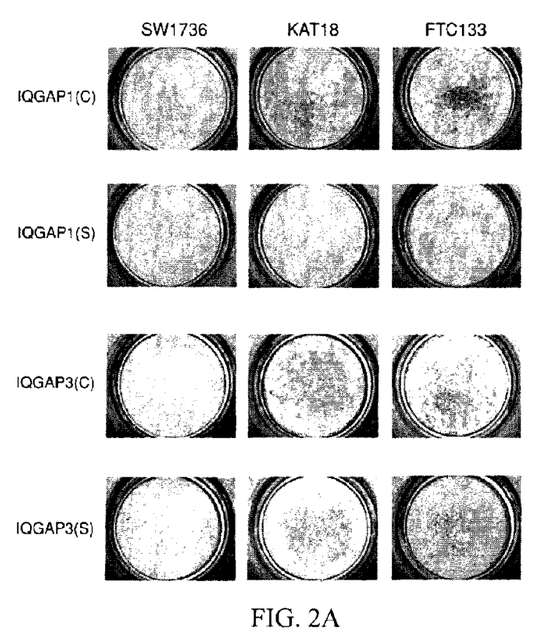
FIG. 2A shows representative results on the invasion assay of three thyroid cancer cells.
Figure 2B:
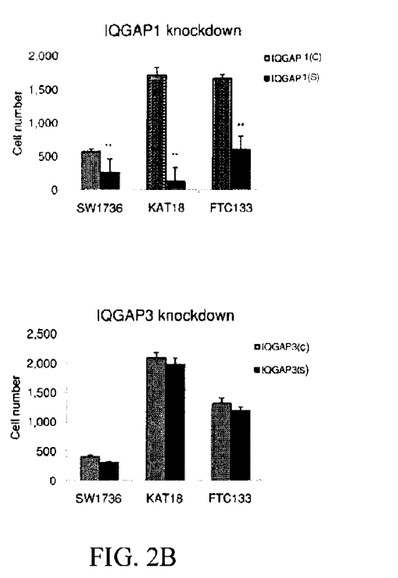

Example 6—Effects of shRNA Knockdown of IQGAP Proteins on the Invasion of Thyroid Cancer Cells As IQGAP1 copy gain was associated with invasiveness and aggressiveness of thyroid cancer in this study (Tables 1 and 2), we next used the Matrigel in vitro system to functionally test whether IQGAP1 played a role in thyroid cancer cell invasion. As shown in FIG. 2, knockdown of IQGAP1 dramatically inhibited the invasion of all the 3 thyroid cancer cells whereas, in contrast, knockdown of IQGAP3 did not have effect on the invasion of these cells. Thus, these data, consistent with the results of clinicopathologic correlation studies (Table 2), functionally show and confirm the specific and important role of IQGAP1 in the invasiveness of thyroid cancer.

Figure 3A:
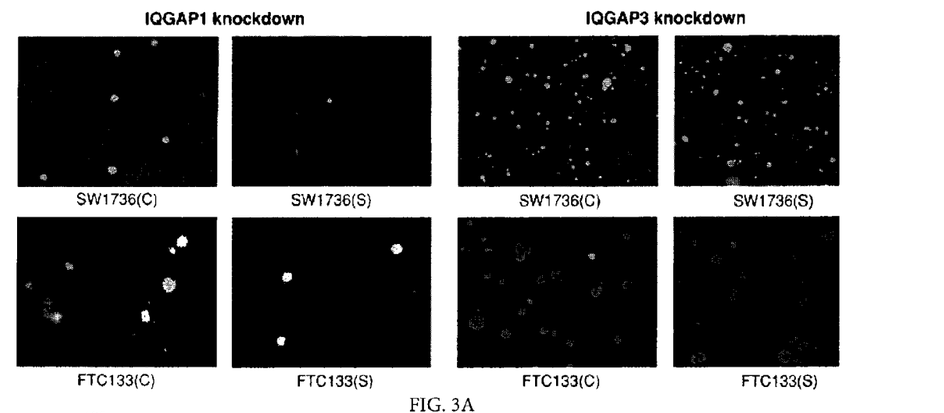
FIG. 3A, representative results of colony formation of SW1736 and FTC133 cells.
Figure 3B:
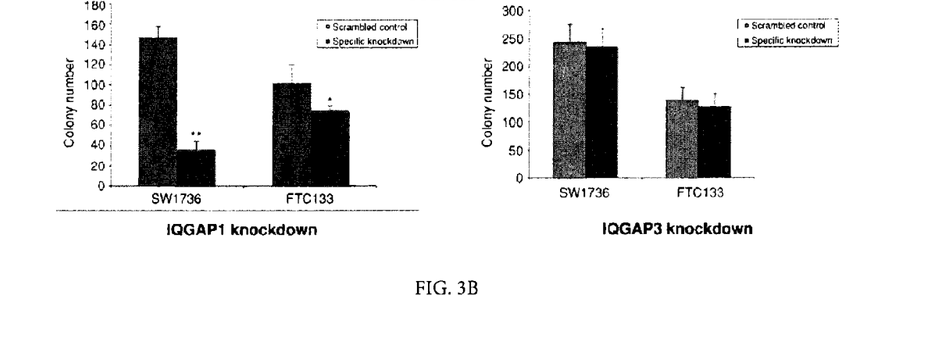
FIG. 3B, histogram plots of colony numbers corresponding to A for each cell type. Only cell colonies containing more than 50 cells were counted. KAT18 cells did not grow on soft agar. "(C)", cell transfection with shRNA containing scrambled nucleotides; "(S)", cell transfection with specific shRNA to knock down IQGAP1 or IQGAP3. *, P<0.05; **, P<0.01.
Figure 4A:
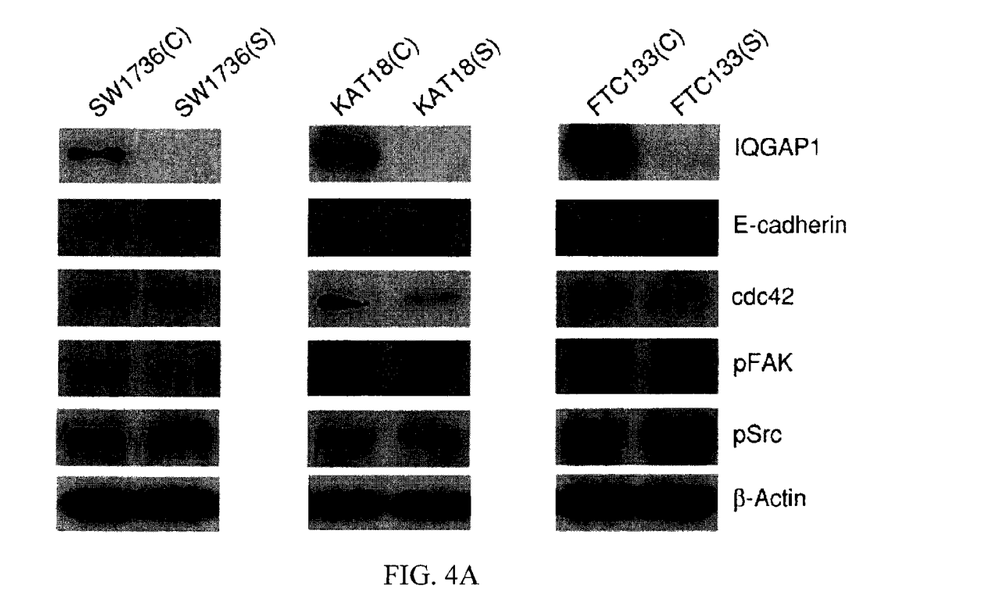
FIG. 4A shows the western blotting analysis of the levels of IQGAP1, E-cadherin, cdc42, phosphorylated FAK (pFAK), phosphorylated Src (pSrc), and β-actin before and after IQGAP1 knockdown. Specific and virtually complete knockdown of IQGAP1 was seen in all the three cells. All other indicated proteins were expressed in all the cells except for E-cadherin, which was expressed only in SW1736 cells. An interesting upregulation of E-cadherin after the knockdown of IQGAP1 was seen in SW1736 cells.
Figure 4B:
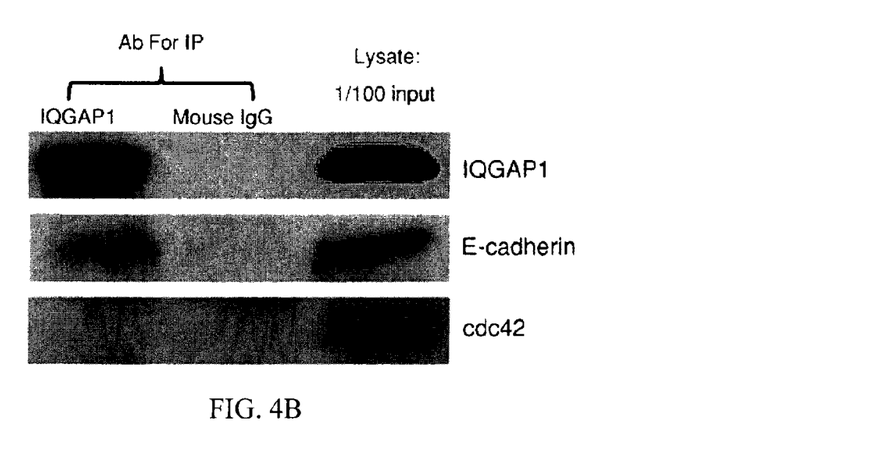
FIG. 4B shows the IP of cell lysates from normal wild-type SW1736 cells using anti-IQGAP1 antibodies, followed by Western blotting of the immunoprecipitates with antibodies against the indicated proteins. Specific co-IP of E-cadherin, but not cdc42, with IQGAP1 was seen. This only occurred with specific monoclonal anti-IQGAP1 antibodies but not nonspecific control mouse IgG. "C", cell transfection with shRNA containing scrambled nucleotides; "S", cell transfection with specific shRNA to knock down IQGAP1. "Input" using 1/100 of the amount of lysates used for IP was directly run for immunoblotting analysis as control to show the proteins of interest

Example 7—Effects of shRNA Knockdown of IQGAP Proteins on Anchorage-Independent Colony Formation of Thyroid Cancer Cells Cell colony formation and expansion on soft agar requires cells to invade and migrate peripherally. We therefore reasoned that, unlike cell proliferation in normal culture medium, colony formation on soft agar could be affected by interfering with IQGAP1 if the latter was important to thyroid cancer cell invasion. Indeed, as shown in FIG. 3, cells with specific IQGAP1 knockdown formed anchorage-independent colonies in soft agar with smaller size or number compared with cells transfected with control shRNA expressing scrambled nucleotides. This was seen in both SW1736 and FTC133 cells, somehow with a more profound effect was seen in the former cells. In contrast, specific knockdown of IQGAP3 showed no effect on colony formation of the 2 cells (FIG. 4). KAT18 cells, whether wild-type, control, or specific shRNA transfection, did not grow on soft agar under our conditions (data not shown).

Example 8—Direct Interaction of IQGAP1 with E-Cadherin in Thyroid Cancer Cells We also investigated the relationship of IQGAP1 with several molecules that had been known to be involved in cancer cell adhesion, invasion, and progression. Among these was E-cadherin, a calcium-dependent adhesion molecule, which was well known for its important role in cell-cell adherence and its deficiency caused cell migration and invasion in cancers (31). As shown in FIG. 4A, the expression of E-cadherin was normal in SW1736 cells but naturally silenced in KAT18 and FTC133. Interestingly, the protein level of E-cadherin in SW1736 cells was significantly upregulated with knockdown of IQGAP1, suggesting that IQGAP1 normally interacts with E-cadherin to down-regulate it and weaken the cell adherence system, thus promoting cell migration and invasion. In contrast, the expression of cdc42 was not affected by knockdown of IQGAP1 (FIG. 4A), suggesting that the change in E-cadherin was specific. Similarly, IQGAP1 knockdown had no effect on the phosphorylation of focal adhesion kinase (FAK) and Src, which were both previously suggested to play a role in thyroid cancer cell invasion and migration (ref 32; FIG. 4A).

To show a direct interaction of IQGAP1 with E-cadherin, we carried out co-IP assay for the two in SW1736 cells. As shown in FIG. 4B, E-cadherin showed up in the precipitates when immunoprecipitated with IQGAP1 antibodies but not with control nonspecific IgG antibodies, showing that these 2 proteins directly interact and complex with each other in thyroid cancer cells. In contrast, co-IP using IQGAP1 antibodies failed to show a band of cdc42, suggesting the lack of direct interaction between IQGAP1 and cdc42 in thyroid cancer cells (FIG. 4B). This result also suggests that the interaction of IQGAP1 with E-cadherin was a specific event. However, the results on the relationship between IQGAP1 and cdc42 do not rule out the possibility that the activity of cdc42, not the protein level, could be affected by IQGAP1.

REFERENCES

The disclosure of each reference cited is expressly incorporated herein.

1. Briggs M W, et al., IQGAP proteins are integral components of cytoskeletal regulation. EMBO Rep 2003; 4:571-4.
2. Nojima H, et al., IQGAP3 regulates cell proliferation through the Ras/ERK signalling cascade. Nat Cell Biol 2008; 10:971-8.
3. Johnson M, et al., IQGAP1 regulation and roles in cancer. Cell Signal 2009; 21:1471-8.
4. White C D, et al., IQGAPs in cancer: a family of scaffold proteins underlying tumorigenesis. FEBS Lett 2009; 583: 1817-24.
5. Ho Y D, et al., et al., IQGAP1 integrates Ca2+/calmodulin and Cdc42 signaling. J Biol Chem 1999; 274:464-70.
6. Brown M D et al., IQGAP1 in cellular signaling: bridging the GAP. Trends Cell Biol 2006; 16:242-9.
7. Weissbach L, et al. Identification of a human rasGAP-related protein containing calmodulin-binding motifs. J Biol Chem 1994; 269:20517-21.
8. Roy M, et al., IQGAP1 binds ERK2 and modulates its activity. J Biol Chem 2004; 279:17329-37.
9. Roy M, et al., IQGAP1 is a scaffold for mitogen-activated protein kinase signaling. Mol Cell Biol 2005; 25:7940-52.
10. Ren J G, et al., IQGAP1 modulates activation of B-Raf. Proc Natl Acad Sci USA 2007; 104:10465-9.
11. Sugimoto N, et al. IQGAP1, a negative regulator of cell-cell adhesion, is upregulated by gene amplification at 15q26 in gastric cancer cell lines HSC39 and 40A. J Hum Genet 2001; 46:21-5.
12. Nabeshima K, et al. Immunohistochemical analysis of IQGAP1 expression in human colorectal carcinomas: its overexpression in carcinomas and association with invasion fronts. Cancer Lett 2002; 176:101-9.
13. Dong P, et al. Overexpression and diffuse expression pattern of IQGAP1 at invasion fronts are independent prognostic parameters in ovarian carcinomas. Cancer Lett 2006; 243:120-7.
14. Altekruse S F, et al. editors. SEER Cancer Statistics Review, 1975-2007, National Cancer Institute. Bethesda, Md.; 2010. based on November 2009 SEER data submission, posted to the SEER web site.
15. Riesco-Eizaguirre G, et al., Molecular biology of thyroid cancer initiation. Clin Transl Oncol 2007; 9:686-93.
16. Xing M, Recent advances in molecular biology of thyroid cancer and their clinical implications. Otolaryngol Clin North Am 2008; 41:1135-46.
17. Sobrinho-Simões M, et al., Intragenic mutations in thyroid cancer. Endocrinol Metab Clin North Am 2008; 37:333-62.
18. Hundahl S A, et al., A National Cancer Data Base report on 53,856 cases of thyroid carcinoma treated in the U.S., 1985-1995. Cancer 1998; 83:2638-48.
19. Verburg F A, et al., Histology does not influence prognosis in differentiated thyroid carcinoma when accounting 20. Zidan J, et al., Pure versus follicular variant of papillary thyroid carcinoma: clinical features, prognostic factors, treatment, and survival. Cancer 2003; 97:1181-5.
21. Xing M., BRAF mutation in papillary thyroid cancer: pathogenic role, molecular bases, and clinical implications. Endocr Rev 2007; 28:742-62.
22. Xing M Prognostic utility of BRAF mutation in papillary thyroid cancer. Mol Cell Endocrinol 2010; 321:86-93.
23. Hou P, et al. Genetic alterations and their relationship in the phosphatidylinositol 3-kinase/Akt pathway in thyroid cancer. Clin Cancer Res 2007; 13:1161-70.
24. Wu G, et al. Uncommon mutation, but common amplifications, of the PIK3CA gene in thyroid tumors. J Clin Endocrinol Metab 2005; 90:4688-93.
25. Liu Z, et al. Highly prevalent genetic alterations in receptor tyrosine kinases and phosphatidylinositol 3-kinase/akt and mitogen-activated protein kinase pathways in anaplastic and follicular thyroid cancers. J Clin Endocrinol Metab 2008; 93:3106-16.
26. Hou P, et al. Induction of thyroid gene expression and radioiodine uptake in melanoma cells: novel therapeutic implications. PLoS One 2009; 4:e6200.
27. Ventura A, et al. Cre-lox-regulated conditional RNA interference from transgenes. Proc Natl Acad Sci USA 2004; 101:10380-5.
28. Liu D, BRAF V600E maintains proliferation, transformation, and tumorigenicity of BRAF-mutant papillary thyroid cancer cells. J Clin Endocrinol Metab 2007; 92:2264-71.
29. Morris L E, et al., Nucleotide variants within the IQGAP1 gene in diffuse-type gastric cancers. Genes Chromosomes Cancer 2005; 42:280-6.
30. Schweppe R E, et al. Deoxyribonucleic acid profiling analysis of 40 human thyroid cancer cell lines reveals cross-contamination resulting in cell line redundancy and misidentification. J Clin Endocrinol Metab. 2008; 93:4331-41.
31. Mărgineanu E, et al., Correlation between E-cadherin abnormal expressions in different types of cancer and the process of metastasis. Rev Med Chir Soc Med Nat Iasi 2008; 112:432-6.
32. Schweppe R E, et al., Inhibition of Src with AZD0530 reveals the Src-Focal Adhesion kinase complex as a novel therapeutic target in papillary and anaplastic thyroid cancer. J Clin Endocrinol Metab 2009; 94:2199-203.
33. Abubaker J, et al. Clinicopathological analysis of papillary thyroid cancer with PIK3CA alterations in a Middle Eastern population. J Clin Endocrinol Metab 2008; 93:611-8.
34. Kuroda S, et al. Role of IQGAP1, a target of the small GTPases Cdc42 and Rac1, in regulation of E-cadherin-mediated cell-cell adhesion. Science 1998; 281:832-5.
35. Gottardi C J, et al., E-cadherin suppresses cellular transformation by inhibiting beta-catenin signaling in an adhesion-independent manner. J Cell Biol 2001; 153:1049-60.

The invention claimed is:

1. A method for predicting aggressiveness of follicular thyroid cancer (FTC) in a human patient comprising the steps of:
   (a) performing quantitative real-time polymerase chain reaction (PCR) on genomic DNA obtained from a patient thyroid tissue sample using primers that will specifically amplify the IQ motif containing GTPase activating protein 1 (IQGAP1) gene, wherein the primers are selected from the group consisting of SEQ ID NO:9 and SEQ ID NO:17, SEQ ID NO:10 and SEQ ID NO:18, SEQ ID NO:11 and SEQ ID NO:19, SEQ ID NO:12 and SEQ ID NO:20, and SEQ ID NO:13 and SEQ ID NO:21;
   (b) detecting an increased copy number gain of the IQGAP1 gene of at least 3 relative to the IQGAP1 copy number in normal thyroid tissue or relative to the copy number of a reference gene in the tissue sample; and
   (c) predicting aggressiveness of FTC in the human patient based on the copy number gain of at least 3 detected in step (b).

* * * * *

```
                         SEQUENCE LISTING

<160> NUMBER OF SEQ ID NOS: 32

<210> SEQ ID NO 1
<211> LENGTH: 19
<212> TYPE: DNA
<213> ORGANISM: Artificial Sequence
<220> FEATURE:
<223> OTHER INFORMATION: shRNA target sequence for IQGAP1, nt 763-781 of
      cDNA with translation start site set at +1

<400> SEQUENCE: 1
gcatccactt accaggata                                                  19

<210> SEQ ID NO 2
<211> LENGTH: 19
<212> TYPE: DNA
<213> ORGANISM: Artificial Sequence
<220> FEATURE:
<223> OTHER INFORMATION: scrambled control for shRNA target

<400> SEQUENCE: 2
gccacccata gaaatttcg                                                  19

<210> SEQ ID NO 3
<211> LENGTH: 19
<212> TYPE: DNA
<213> ORGANISM: Artificial Sequence
<220> FEATURE:
<223> OTHER INFORMATION: shRNA target for IQGAP3, nt 4004-4023

<400> SEQUENCE: 3
ggacctgagc aagctagaa                                                  19

<210> SEQ ID NO 4
```

```
<211> LENGTH: 19
<212> TYPE: DNA
<213> ORGANISM: Artificial Sequence
<220> FEATURE:
<223> OTHER INFORMATION: scrambled control for IQGAP3 shRNA

<400> SEQUENCE: 4
gccaacggac gtaatgaag                                                   19

<210> SEQ ID NO 5
<211> LENGTH: 9
<212> TYPE: DNA
<213> ORGANISM: Artificial Sequence
<220> FEATURE:
<223> OTHER INFORMATION: part of construct for shRNA

<400> SEQUENCE: 5 ttcaagaga                                                               9

<210> SEQ ID NO 6
<211> LENGTH: 7
<212> TYPE: DNA
<213> ORGANISM: Artificial Sequence
<220> FEATURE:
<223> OTHER INFORMATION: part of construct for shRNA

<400> SEQUENCE: 6 tttttc                                                                  7

<210> SEQ ID NO 7
<211> LENGTH: 11
<212> TYPE: DNA
<213> ORGANISM: Artificial Sequence
<220> FEATURE:
<223> OTHER INFORMATION: part of construct for shRNA

<400> SEQUENCE: 7
tcgagaaaaa a                                                           11

<210> SEQ ID NO 8
<211> LENGTH: 9
<212> TYPE: DNA
<213> ORGANISM: Artificial Sequence
<220> FEATURE:
<223> OTHER INFORMATION: part of construct for shRNA

<400> SEQUENCE: 8 tctcttgaa                                                               9

<210> SEQ ID NO 9
<211> LENGTH: 20
<212> TYPE: DNA
<213> ORGANISM: Artificial Sequence
<220> FEATURE:
<223> OTHER INFORMATION: forward primer for IQGAP1, exon 19

<400> SEQUENCE: 9
tgcatccatt cttgcctgtg                                                  20

<210> SEQ ID NO 10
<211> LENGTH: 24
<212> TYPE: DNA
<213> ORGANISM: Artificial Sequence
<220> FEATURE:
<223> OTHER INFORMATION: forward primer for IQGAP1, exon 20-22

<400> SEQUENCE: 10
```
ttgatgcttg ggaagtaata tgtc                                              24

<210> SEQ ID NO 11
<211> LENGTH: 24
<212> TYPE: DNA
<213> ORGANISM: Artificial Sequence
<220> FEATURE:
<223> OTHER INFORMATION: forward primer for IQGAP1, exon 23

<400> SEQUENCE: 11
agacaatgct atttcctgag acgt                                              24

<210> SEQ ID NO 12
<211> LENGTH: 24
<212> TYPE: DNA
<213> ORGANISM: Artificial Sequence
<220> FEATURE:
<223> OTHER INFORMATION: forward primer for IQGAP1, exon 29

<400> SEQUENCE: 12
tgtttcgtct gttccagatt attg                                              24

<210> SEQ ID NO 13
<211> LENGTH: 21
<212> TYPE: DNA
<213> ORGANISM: Artificial Sequence
<220> FEATURE:
<223> OTHER INFORMATION: forward primer for IQGAP1, exon 29

<400> SEQUENCE: 13
ttgttgctcc tgatgccttt g                                                 21

<210> SEQ ID NO 14
<211> LENGTH: 19
<212> TYPE: DNA
<213> ORGANISM: Artificial Sequence
<220> FEATURE:
<223> OTHER INFORMATION: forward primer for IQGAP3, exon 19

<400> SEQUENCE: 14
agctctggaa agccaacgt                                                    19

<210> SEQ ID NO 15
<211> LENGTH: 20
<212> TYPE: DNA
<213> ORGANISM: Artificial Sequence
<220> FEATURE:
<223> OTHER INFORMATION: forward primer for TMEM84, exon 3

<400> SEQUENCE: 15
ggtgatgggc aggataagag                                                   20

<210> SEQ ID NO 16
<211> LENGTH: 25
<212> TYPE: DNA
<213> ORGANISM: Artificial Sequence
<220> FEATURE:
<223> OTHER INFORMATION: forward primer for beta-actin exon 4

<400> SEQUENCE: 16
tcacccacac tgtgcccatc tacga                                             25

<210> SEQ ID NO 17
<211> LENGTH: 21
<212> TYPE: DNA

```
<213> ORGANISM: Artificial Sequence
<220> FEATURE:
<223> OTHER INFORMATION: reverse primer for IQGAP1, exon 19

<400> SEQUENCE: 17
tgaccgttta ttacccctgc t                                        21

<210> SEQ ID NO 18
<211> LENGTH: 23
<212> TYPE: DNA
<213> ORGANISM: Artificial Sequence
<220> FEATURE:
<223> OTHER INFORMATION: reverse  primer for IQGAP1, exon 20-22

<400> SEQUENCE: 18
aaagaggtct gtggagaata ccc                                      23

<210> SEQ ID NO 19
<211> LENGTH: 22
<212> TYPE: DNA
<213> ORGANISM: Artificial Sequence
<220> FEATURE:
<223> OTHER INFORMATION: reverse primer for IQGAP1, exon 23

<400> SEQUENCE: 19
gctcttatgg cagtagctga gg                                       22

<210> SEQ ID NO 20
<211> LENGTH: 24
<212> TYPE: DNA
<213> ORGANISM: Artificial Sequence
<220> FEATURE:
<223> OTHER INFORMATION: reverse primer for IQGAP1, exon 29

<400> SEQUENCE: 20
tccacagact ctcttaagca cttg                                     24

<210> SEQ ID NO 21
<211> LENGTH: 20
<212> TYPE: DNA
<213> ORGANISM: Artificial Sequence
<220> FEATURE:
<223> OTHER INFORMATION: reverse primer for IQGAP1, exon 29

<400> SEQUENCE: 21
gcaatggagc ccagatttcg                                          20

<210> SEQ ID NO 22
<211> LENGTH: 20
<212> TYPE: DNA
<213> ORGANISM: Artificial Sequence
<220> FEATURE:
<223> OTHER INFORMATION: reverse  primer for IQGAP3, exon 19

<400> SEQUENCE: 22
cctcagaaag tgggaatgct                                          20

<210> SEQ ID NO 23
<211> LENGTH: 19
<212> TYPE: DNA
<213> ORGANISM: Artificial Sequence
<220> FEATURE:
<223> OTHER INFORMATION: reverse primer for TMEM84, exon 3

<400> SEQUENCE: 23
ccttccaggt gaggaatcg                                           19
```

<210> SEQ ID NO 24
<211> LENGTH: 23
<212> TYPE: DNA
<213> ORGANISM: Artificial Sequence
<220> FEATURE:
<223> OTHER INFORMATION: reverse primer for beta-actin exon 4

<400> SEQUENCE: 24
tcggtgagga tcttcatgag gta                                    23

<210> SEQ ID NO 25
<211> LENGTH: 21
<212> TYPE: DNA
<213> ORGANISM: Artificial Sequence
<220> FEATURE:
<223> OTHER INFORMATION: sequencing primer for IQGAP1, exon 19

<400> SEQUENCE: 25
tgaccgttta ttacccctgc t                                      21

<210> SEQ ID NO 26
<211> LENGTH: 23
<212> TYPE: DNA
<213> ORGANISM: Artificial Sequence
<220> FEATURE:
<223> OTHER INFORMATION: sequencing primer for IQGAP1, exon 20-22

<400> SEQUENCE: 26
aaagaggtct gtggagaata ccc                                    23

<210> SEQ ID NO 27
<211> LENGTH: 24
<212> TYPE: DNA
<213> ORGANISM: Artificial Sequence
<220> FEATURE:
<223> OTHER INFORMATION: sequencing primer for IQGAP1, exon 23

<400> SEQUENCE: 27
agacaatgct atttcctgag acgt                                   24

<210> SEQ ID NO 28
<211> LENGTH: 24
<212> TYPE: DNA
<213> ORGANISM: Artificial Sequence
<220> FEATURE:
<223> OTHER INFORMATION: sequencing primer for IQGAP1, exon 29

<400> SEQUENCE: 28
tgtttcgtct gttccagatt attg                                   24

<210> SEQ ID NO 29
<211> LENGTH: 20
<212> TYPE: DNA
<213> ORGANISM: Artificial Sequence
<220> FEATURE:
<223> OTHER INFORMATION: probe IQGAP1, exon 29

<400> SEQUENCE: 29
catcattgac ctgtcagcag                                        20

<210> SEQ ID NO 30
<211> LENGTH: 20
<212> TYPE: DNA
<213> ORGANISM: Artificial Sequence
<220> FEATURE:

```
<223> OTHER INFORMATION: probe for IQGAP3, exon 19

<400> SEQUENCE: 30
ctttgttatc cagctccagg                                              20

<210> SEQ ID NO 31
<211> LENGTH: 20
<212> TYPE: DNA
<213> ORGANISM: Artificial Sequence
<220> FEATURE:
<223> OTHER INFORMATION: probe for TMEM84, exon 3

<400> SEQUENCE: 31
tgtaatttca cctttctccg                                              20

<210> SEQ ID NO 32
<211> LENGTH: 21
<212> TYPE: DNA
<213> ORGANISM: Artificial Sequence
<220> FEATURE:
<223> OTHER INFORMATION: probe for beta-actin, exon 4

<400> SEQUENCE: 32
atgccctccc ccatgccatc c                                            21
```